(12) United States Patent
Bhattacharya et al.

(10) Patent No.: US 10,055,839 B2
(45) Date of Patent: Aug. 21, 2018

(54) LEVERAGING ON LOCAL AND GLOBAL TEXTURES OF BRAIN TISSUES FOR ROBUST AUTOMATIC BRAIN TUMOR DETECTION

(71) Applicant: SIEMENS AKTIENGESELLSCHAFT, München (DE)

(72) Inventors: Subhabrata Bhattacharya, Edison, NJ (US); Shanhui Sun, Plainsboro, NJ (US); Terrence Chen, Princeton, NJ (US); Ali Kamen, Skillman, NJ (US)

(73) Assignee: SIEMENS AKTIENGESELLSCHAFT, München (DE)

( * ) Notice: Subject to any disclaimer, the term of this patent is extended or adjusted under 35 U.S.C. 154(b) by 251 days.

(21) Appl. No.: 15/061,465

(22) Filed: Mar. 4, 2016

(65) Prior Publication Data
US 2017/0256052 A1    Sep. 7, 2017

(51) Int. Cl.
*G06K 9/00* (2006.01)
*G06T 7/00* (2017.01)
(Continued)

(52) U.S. Cl.
CPC ........ *G06T 7/0012* (2013.01); *A61B 1/00045* (2013.01); *A61B 1/04* (2013.01);
(Continued)

(58) Field of Classification Search
CPC ... G06T 7/0012; G06T 7/401; G06K 9/00147; G06K 9/4642; G06K 9/6292; G06K 9/6218; G06K 9/52; G06K 9/6267; A61B 5/7282; A61B 1/00045; A61B 1/04; A61B 5/4064; H04N 19/136; H04N 19/124
See application file for complete search history.

(56) References Cited

U.S. PATENT DOCUMENTS

| 2004/0015462 A1* | 1/2004 | Lienhart | G06K 9/6269 |
| | | | 706/45 |
| 2011/0208176 A1* | 8/2011 | Mardirossian | A61B 18/18 |
| | | | 606/33 |

(Continued)

FOREIGN PATENT DOCUMENTS

WO    2015195609    12/2015

OTHER PUBLICATIONS

PCT International Search Report dated May 23, 2017; International Application No. PCT/US2017/017798; Filing Date: Feb. 14, 2017; 17-pages.

(Continued)

*Primary Examiner* — Andrew Moyer

(57) ABSTRACT

A method for performing cellular classification includes generating a plurality of local dense Scale Invariant Feature Transform (SIFT) features based on a set of input images and converting the plurality of local dense SIFT features into a multi-dimensional code using a feature coding process. A first classification component is used to generate first output confidence values based on the multi-dimensional code and a plurality of global Local Binary Pattern Histogram (LBP-H) features are generated based on the set of input images. A second classification component is used to generate second output confidence values based on the plurality of LBP-H features and the first output confidence values and the second output confidence values are merged. Each of the set of input images may then be classified as one of a plurality of cell types using the merged output confidence values.

19 Claims, 5 Drawing Sheets

(51) Int. Cl.
  H04N 19/124    (2014.01)
  H04N 19/136    (2014.01)
  A61B 1/00      (2006.01)
  A61B 1/04      (2006.01)
  A61B 5/00      (2006.01)
  G06K 9/46      (2006.01)
  G06K 9/52      (2006.01)
  G06K 9/62      (2006.01)
  G06T 7/40      (2017.01)

(52) U.S. Cl.
  CPC .......... *A61B 5/4064* (2013.01); *A61B 5/7282* (2013.01); *G06K 9/00147* (2013.01); *G06K 9/4642* (2013.01); *G06K 9/4671* (2013.01); *G06K 9/4676* (2013.01); *G06K 9/52* (2013.01); *G06K 9/6218* (2013.01); *G06K 9/6262* (2013.01); *G06K 9/6267* (2013.01); *G06K 9/6292* (2013.01); *G06T 7/401* (2013.01); *H04N 19/124* (2014.11); *H04N 19/136* (2014.11); *G06K 9/6269* (2013.01); *G06K 9/6282* (2013.01); *G06K 2009/4666* (2013.01); *G06T 2207/30016* (2013.01)

(56) References Cited

U.S. PATENT DOCUMENTS

2012/0306934 A1* 12/2012 Ohashi ................ G09G 5/34
                                                    345/684
2017/0213339 A1* 7/2017 Hibbard ............... G06T 7/0012
2017/0342500 A1* 11/2017 Marquard ............ C12Q 1/6886

OTHER PUBLICATIONS

Shaohua Wan et al: "Towards an Efficient Computational Framework for Guiding Surgical Resection through Intra-operative Endomicroscopic Pathology" In: "Network and Parallel Computing" Jan. 1, 2015 (Jan. 1, 2015), Springer International Publishing, Cham 032548, XP55233936, ISSN: 0302-9743 ISBN: 978-3-642-37634-4 / Jan. 1, 2015.

Ling Ma et al: "A new classifier fusion method based on historical and on-line classification reliability for recognizing common CT imaging signs of lung diseases", Computerized Medical Imaging and Graphics, vol. 40, Mar. 1, 2015 (Mar. 1, 2015), pp. 39-48, XP055371491, US ISSN: 0895-6111, DOI / Jan. 3, 2015.

Ali Kamen et al: "Automatic Tissue Differentiation Based on Confocal Endomicroscopic Images for Intraoperative Guidance in Neurosurgery". Biomed Research International. vol. 2016. Jan. 18, 2016 (Jan. 18, 2016). pp. 1-8. XP055263355 / Jan. 18, 2016.

Tax D M J et al: "Combining multiple classifiers by averaging or by multiplying?", Pattern Recognition, Elsevier, GB, vol. 33, No. 9, Sep. 1, 2000 (Sep. 1, 2000), pp. 1475-1485, XP004243900, ISSN: 0031-3203, DOI.

Alexandre L A et al: "On combining classifiers using sum and product rules", Pattern Recognition Letters, Elsevier, Amsterdam, NL, vol. 22, No. 12, Oct. 1, 2001 (Oct. 1, 2001), pp. 1283-1289, XP027301738, ISSN: 0167-8655.

* cited by examiner

LEVERAGING ON LOCAL AND GLOBAL TEXTURES OF BRAIN TISSUES FOR ROBUST AUTOMATIC BRAIN TUMOR DETECTION

TECHNICAL FIELD

The present disclosure relates generally to methods, systems, and apparatuses for leveraging local and global textures of brain tissues for robust automatic brain tumor detection. In addition, the proposed technology may be applied to a variety of other cellular image classification tasks.

BACKGROUND

Glioblastoma is the most predominant and most aggressive malignant brain tumor in humans, accounting for 52% of all brain tumor cases and 20% of all intracranial tumors. Meningioma, on the other hand, although benign, accounts for more than 35% of primary brain tumors in the United States, and occurs in approximately 7 of every 100,000 people, with an approximate 5 year survival timeline of the diagnosed patient. Optimal surgical resection is primarily based on accurate detection of tumor tissue during the resection procedure.

Recently, Confocal Laser Endomicroscopy (CLE) has emerged as a promising in-vivo imaging technology that allows real-time examination of body tissues on a scale that was previously only possible on histologic slices. Neurosurgeons could now use CLE as a surgical guidance tool for brain tumors. However, as a manual examination task, this can be highly time-consuming and error-prone. Thus, there has been an increasing demand in employing computer vision techniques for brain tumor tissue typing and pathology in the CLE probing process.

Tissues affected by Glioblastoma and Meningioma, are usually characterized by sharp granular and smooth homogeneous patterns, respectively. However, the low resolution of current CLE imaging systems, coupled with the presence of both kinds of patterns in the probing area, makes it extremely challenging for common image classification algorithms. Besides the great variability between images from the same tumor class, the differences between the two classes of tumors are not clearly evident when both granular and homogeneous patterns are present in the image.

CLE technology itself being at a nascent stage, there are only a handful of research efforts that address automatic analysis of imagery under this modality. Most prior works in this direction adapt a generic image classification technique based on bag-of-visual words to perform this task. Within this technique, first images containing different tumors are collected and low-level features (characteristic property of an image patch) are extracted from them as part of the training step. From all images in the training set, representative features (also known as visual words) are then obtained using a vocabulary learning method usually either unsupervised clustering or by a supervised dictionary learning technique. After that, each of the collected training images is represented in a unified manner as a bag or collection of visual words in the vocabulary. This is followed by training a classifier to use the unified representation of each image. Given an unlabeled image, features are extracted and the image in turn is represented in terms of already learned visual words. Finally, the representation is input to a pre-trained classifier, which predicts the label of the given image based on its similarity with pre-observed training images.

While conventional cell classification procedures provide adequate results for some cases, they are limited in some applications. For example, because different kinds of brain tumors are characterized by different textures, it is practically impossible to use one universal feature space that is discriminative for a given tumor class. Thus, it is desired to provide a way to combine feature spaces to capture these salient attributes from different tumor classes more effectively.

SUMMARY

Embodiments of the present invention address and overcome one or more of the above shortcomings and drawbacks, by providing methods, systems, and apparatuses related to leveraging local and global textures of brain tissues for robust automatic brain tumor detection. Briefly, the techniques described herein may be used to provide a sustainable and extensible software system for automatic classification of different kinds of brain tumors as imaged under endomicroscopic probes. Such a technology could potentially assist surgeons to examine brain tissues on a histological scale in real-time during the operation. Typically, it is a challenging task for neurosurgeons to interpret these images in real-time, primarily due to the low signal to noise ratio and variability in the patterns expressed within these images by various examined tissue types. However, the techniques described herein leverage information contained in structural properties of different kinds of tumors and integrate this knowledge in an efficient computational framework that can be used to classify different types of brain tumors in real-time with increased accuracy over conventional techniques. The examples provided herein are directed at brain tumor endomicroscopy images. However, it should be understood that the techniques described herein may be applied similarly to the classification of other types of medical images, or even natural images.

According to some embodiments, a method for performing cellular classification includes generating a plurality of local dense Scale Invariant Feature Transform (SIFT) features based on a set of input images and converting the plurality of local dense SIFT features into a multi-dimensional code using a feature coding process. A first classification component is used to generate first output confidence values based on the multi-dimensional code and a plurality of global Local Binary Pattern Histogram (LBP-H) features are generated based on the set of input images. A second classification component is used to generate second output confidence values based on the plurality of LBP-H features and the first output confidence values and the second output confidence values are merged (e.g., using a multiplicative fusion algorithm). Each of the set of input images may then be classified as one of a plurality of cell types using the merged output confidence values.

In some embodiments, the aforementioned method further includes generating the set of images based on a plurality of input images (e.g., images acquired using an endomicroscopy or digital holographic microscopy device during a medical procedure). Additionally, in some embodiments, the entropy of each input image may be used to exclude certain low entropy images ("entropy" being representative of an amount of texture information in a respective image). For example, in one embodiment, an entropy value is calculated for each of the input images. Next, low-entropy images are identified in the set of input images. These low-entropy images are each associated with a respective entropy value below a threshold value (e.g., pre-set by the user). The low-entropy acquired images may then be excluded from further processing.

Regarding the feature coding process used in the aforementioned method, various feature coding processes generally known in the art may be adapted for use with the particular features of the method. For example, in some embodiments, bag of words coding process is performed by randomly selecting a predetermined percentage of descriptors from a training split and performing k-means clustering to construct a plurality of different vocabularies. The different vocabularies are used to quantize the SIFT features in each input image included in the set of input images to yield a quantized representation of the SIFT features, wherein the multi-dimensional code is the quantized representation.

Various types of classifiers generally known in the art may be adapted for use in the classification component employed by the aforementioned method. For example, in one embodiment, the first classification component applies a Support Vector Machine (SVM) classifier and the multi-dimensional code is a linear or a radial basis function (RBF) kernel. The same type of classifier may be used for both classification components employed by the aforementioned method or, alternatively, different classifiers may be used. For example, in one embodiment, the first classification component used an SVM classifier, while the second classification component is a Random Forest classifier with a plurality of trees and a maximum depth of a plurality of levels for each of the trees.

According to another embodiment of the present invention, a method for performing cellular classification during a medical procedure includes sub-processes performed before and during the procedure. Prior to the medical procedure, a first classification component is trained based on a plurality of local dense SIFT features associated with a plurality of training images, and a second classification component is trained based on a plurality of global LBP-H features associated with the plurality of training images. During the medical procedure, a cell classification process is performed by acquiring an input image using an endomicroscopy device, using the first classification component to generate first output confidence values based on SIFT features associated with the input image, and using the second classification component to generate second output confidence values based on LBP-H features associated with the input image. Then, the first output confidence values and the second output confidence values are merged and a class label corresponding to the input image may be identified based on the merged output confidence values. Once the class label is determined, it may be presented to a user, for example, on a display operably coupled to the endomicroscopy device. This class label may provide information such as an indication of whether biological material in the input image is healthy, malignant, or benign.

According to another aspect of the present invention, a system performing cellular classification comprises an endomicroscopy device (e.g., a Confocal Laser Endo-microscopy device or Digital Holographic Microscopy (DHM) device), an imaging computer, and a display. The endomicroscopy device is configured to acquire a set of input images during a medical procedure. The imaging computer is configured to perform a cellular classification process during the medical procedure. This cellular classification process may include using a first classification component to generate first output confidence values based on SIFT features associated with the set of input images, and using a second classification component to generate second output confidence values based on LBP-H features associated with the set of input images. Various classifiers may be used including, for example, SVM and Random Forrest Classifiers. The aforementioned process may further include merging the first output confidence values and the second output confidence values, and identifying one or more cellular class labels corresponding to the set of input images based on the merged output confidence values. The display is configured to present the one or more cellular class labels during the medical procedure.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure includes several embodiments directed at methods, systems, and apparatuses related to leveraging local and global textures of brain tissues for robust automatic brain tumor detection. The techniques described herein are based on the observation that different kinds of brain tumors are characterized by different textures. This is demonstrated in FIG. 3 where the top row shows representative frames from Glioblastoma and bottom row from Meningioma cases, captured using CLE imagery. Note how the former is characterized by sharp granular patterns while the latter by smooth homogeneous patterns. Thus, it is practically impossible to use one universal feature space that is discriminative for a given tumor class. Specifically, malignant brain tumors can be identified by sharp granular patterns in brain tissues while the occurrence of its benign variant Meningioma is characterized by smooth homogeneous patterns. Thus, by employing a combination of feature spaces these salient attributes may be captured from different tumor classes effectively.

Regarding the combination of feature spaces employed during image processing, the techniques described herein adapt Local Binary Pattern Histograms (LBP-H) and Dense Scale Invariant Feature Transform (SIFT) features in a computational framework to capture discriminative information from tumor images. The disclosed framework effectively integrates various types of classification algorithms to selectively leverage on the information available from the given feature spaces LBP-H and Dense SIFT. Because these feature spaces capture complementary information, the overall efficiency and efficacy of the method has significant improvement over the algorithms currently used in practice.

Figure 1:
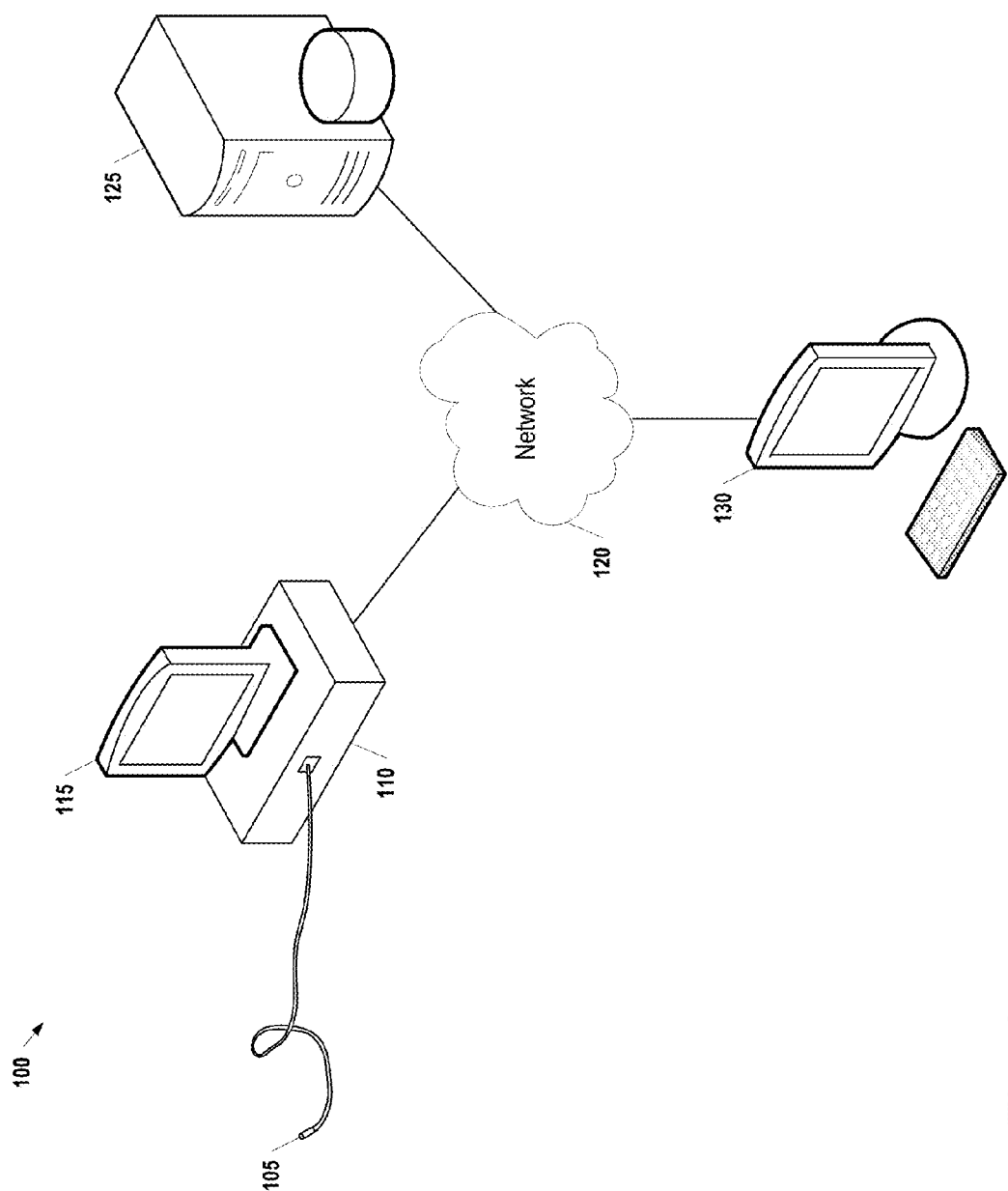
FIG. 1 provides an example of a endomicroscopy-based system which may be used to perform cell classification, according to some embodiments.

FIG. 1 provides an example of an endomicroscopy-based system 100 which may be used to perform cell classification and brain tumor detection, according to some embodiments. Briefly, endomicroscopy is a technique for obtaining histology-like images from inside the human body in real-time through a process known as "optical biopsy." The term "endomicroscopy" generally refers to fluorescence confocal microscopy, although multi-photon microscopy and optical coherence tomography have also been adapted for endoscopic use and may be likewise used in various embodiments. Non-limiting examples of commercially available clinical endomicroscopes include the Pentax ISC-1000/EC3870CIK and Cellvizio (Mauna Kea Technologies, Paris, France). The main applications have traditionally been in imaging the gastro-intestinal tract, particularly for the diagnosis and characterization of Barrett's Esophagus, pancreatic cysts and colorectal lesions. The diagnostic spectrum of confocal endomicroscopy has recently expanded from screening and surveillance for colorectal cancer towards Barrett's esophagus, *Helicobacter pylori* associated gastritis and early gastric cancer. Endomicroscopy enables subsurface analysis of the gut mucosa and in vivo histology during ongoing endoscopy in full resolution by point scanning laser fluorescence analysis. Cellular, vascular and connective structures can be seen in detail. The new detailed images seen with confocal laser endomicroscopy will allow a unique look on cellular structures and functions at and below the surface of the gut. Additionally, as discussed in further detail below, endomicroscopy may also be applied to brain surgery where identification of malignant (glioblastoma) and benign (meningioma) tumors from normal tissues is clinically important.

In the example of FIG. 1, a group of devices are configured to perform Confocal Laser Endo-microscopy (CLE). These devices include a Probe 105 operably coupled to an Imaging Computer 110 and an Imaging Display 115. In FIG. 1, Probe 105 is a confocal miniature probe. However, it should be noted that various types of miniature probes may be used, including probes designed for imaging various fields of view, imaging depths, distal tip diameters, and lateral and axial resolutions. The Imaging Computer 110 provides an excitation light or laser source used by the Probe 105 during imaging. Additionally, the Imaging Computer 110 may include imaging software to perform tasks such as recording, reconstructing, modifying, and/or export images gathered by the Probe 105. The Imaging Computer 110 may also be configured to perform a brain tumor classification, discussed in greater detail below with respect to FIG. 2.

A foot pedal (not shown in FIG. 1) may also be connected to the Imaging Computer 110 to allow the user to perform functions such as, for example, adjusting the depth of confocal imaging penetration, start and stop image acquisition, and/or saving image either to a local hard drive or to a remote database such as Database Server 125. Alternatively or additionally, other input devices (e.g., computer, mouse, etc.) may be connected to the Imaging Computer 110 to perform these functions. The Imaging Display 115 receives images captured by the Probe 105 via the Imaging Computer 110 and presents those images for view in the clinical setting.

Continuing with the example of FIG. 1, the Imaging Computer 110 is connected (either directly or indirectly) to a Network 120. The Network 120 may comprise any computer network known in the art including, without limitation, an intranet or internet. Through the Network 120, the Imaging Computer 110 can store images, videos, or other related data on a remote Database Server 125. Additionally a User Computer 130 can communicate with the Imaging Computer 110 or the Database Server 125 to retrieve data (e.g., images, videos, or other related data) which can then be processed locally at the User Computer 130. For example, the User Computer 130 may retrieve data from either Imaging Computer 110 or the Database Server 125 and use it to perform the Cell Classification Process discussed below in FIG. 2.

Although FIG. 1 shows a CLE-based system, in other embodiments, the system may alternatively use a DHM imaging device. DHM, also known as interference phase microscopy, is an imaging technology that provides the ability to quantitatively track sub-nanometric optical thickness changes in transparent specimens. Unlike traditional digital microscopy, in which only intensity (amplitude) information about a specimen is captured, DHM captures both phase and intensity. The phase information, captured as a hologram, can be used to reconstruct extended morphological information (e.g., depth and surface characteristics) about the specimen using a computer algorithm. Modern DHM implementations offer several additional benefits, such as fast scanning/data acquisition speed, low noise, high resolution and the potential for label-free sample acquisition. While DHM was first described in the 1960s, instrument size, complexity of operation, and cost have been major barriers to widespread adoption of this technology for clinical or point-of-care applications. Recent developments have attempted to address these barriers while enhancing key features, raising the possibility that DHM could be an attractive option as a core, multiple impact technology in healthcare and beyond.

Figure 2:
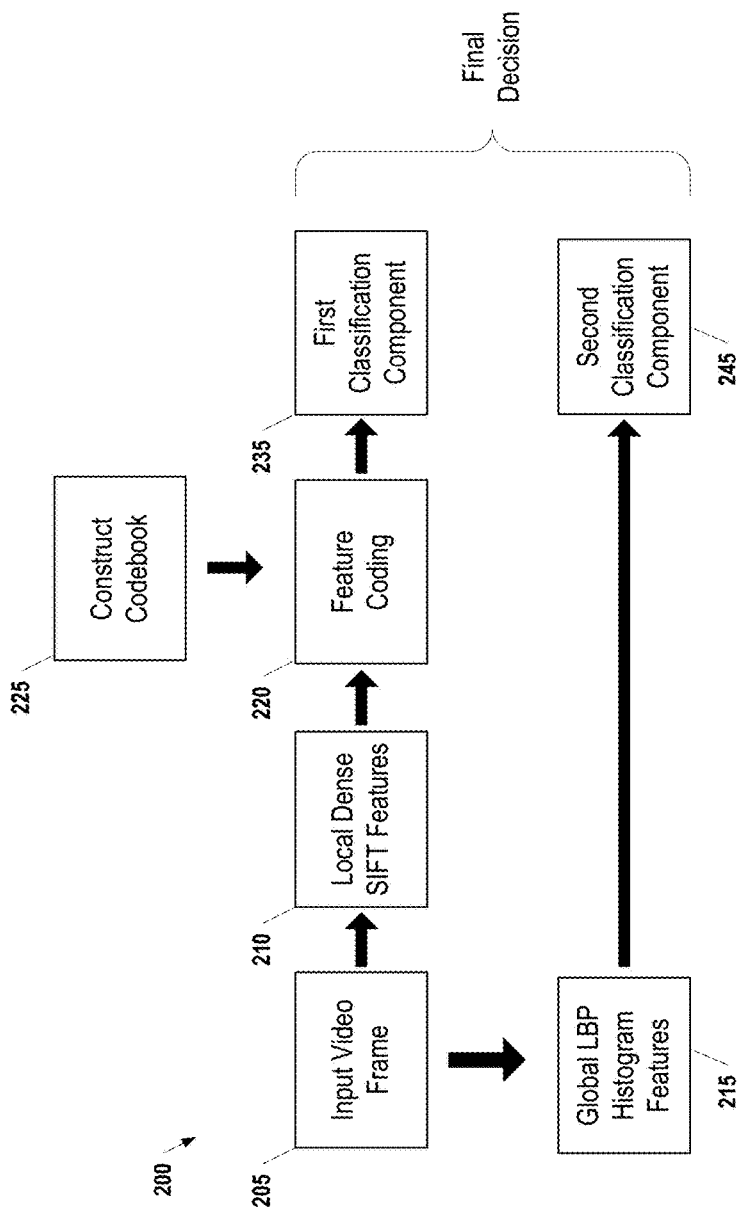
FIG. 2 provides an overview of a brain tumor classification process that may be applied in some embodiments of the present invention.

FIG. 2 provides an overview of a Brain Tumor Classification Process 200 that may be applied in some embodiments of the present invention. The task of automatic brain tumor classification, like all supervised learning tasks, uses a training phase which may be performed off-line. The training phase comprises extracting low-level features from frames from input video sequences. Extracted features are then pooled using an encoding strategy. The classifiers are used to identify one or more class labels for the data based on pre-determined cellular data. These class labels may provide an indication of, for example, whether a particular tissue is malignant or benign. Additionally, in some embodiments, the class label may provide an indication of healthy tissue. Various components for performing the Brain Tumor Classification Process 200 are described in greater detail below, along with some additional optional features which may be applied in some embodiments.

Figure 3:
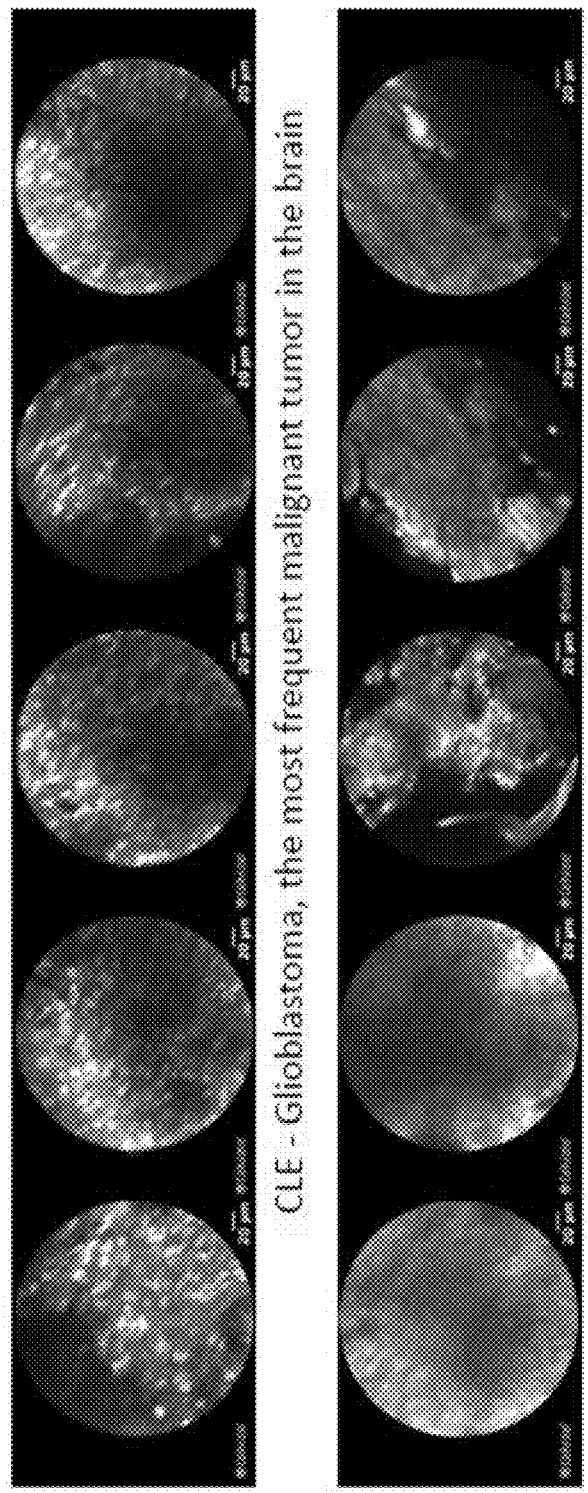
FIG. 3 provides a set of low-entropy and high-entropy images of Glioblastoma and Meningioma.

Prior to the start of the Brain Tumor Classification Process 200, an Entropy-based Image Pruning Component (not shown in FIG. 1) may optionally be used to automatically remove image frames with low image texture information (e.g., low-contrast and contain little categorical information) that may not be clinically interesting or not suitable for image classification. This removal may be used, for example, to address the limited imaging capability of some CLE devices. Image entropy is a quantity which is used to describe the "informativeness" of an image, i.e., the amount of information contained in an image. Low-entropy images have very little contrast and large runs of pixels with the same or similar gray values. On the other hand, high entropy images have a great deal of contrast from one pixel to the next. FIG. 3 provides a set of low-entropy and high-entropy images of Glioblastoma and Meningioma. As shown in the figure, low-entropy images contain a lot of homogeneous image regions, while high-entropy images are characterized by rich image structures.

Figure 4:
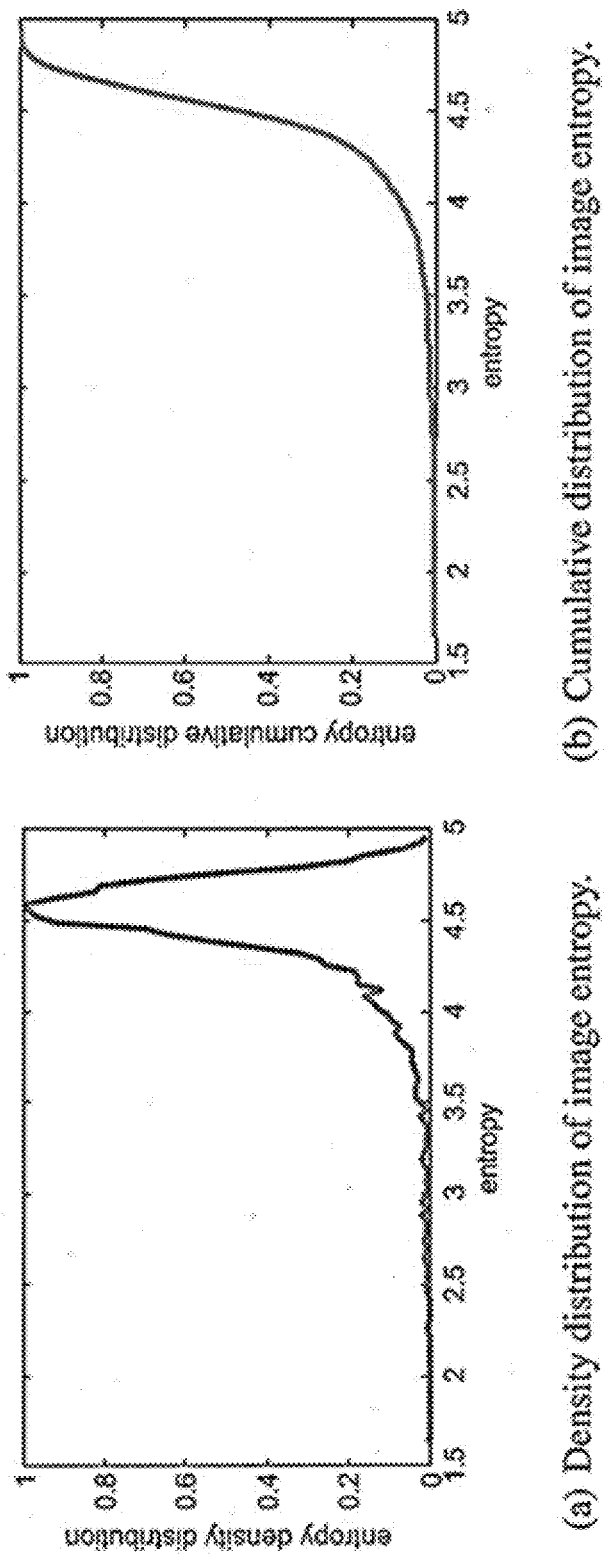
FIG. 4 provides an example of image entropy distribution for images in a brain tumor dataset, as may be utilized in some embodiments.

In some embodiments, the Entropy-based Image Pruning Component performs pruning using an entropy threshold. This threshold may be set based on the distribution of the image entropy throughout the dataset. FIG. 4 provides an example of image entropy distribution for images in a brain tumor dataset, as may be utilized in some embodiments. As can be seen, there is a relatively large number of images whose entropy is significantly lower than that of the rest of the images. Thus, for this example, the entropy threshold can be set such that 10% of images will be discarded from later stages of our system (e.g., 4.05 for data shown in FIG. 4).

Continuing with reference to FIG. 2, features are extracted from each Input Video Frame 205 captured by the biological imaging device. A dense sampling strategy is employed during the feature extraction phase to ensure a fair comparison across all feature descriptors. From each frame, a predetermined number (e.g., 500) of keypoints are uniformly sampled after applying a circular region of interest (approximately of the same radius as the endoscopic lens). Each keypoint is then described using Local Dense Scale Invariant Feature Transform (SIFT) Features 210 and Global Local Binary Patterns (LBP) Histogram Features 215. All of these descriptors capture quantized gradient orientations of pixel intensities in a local neighborhood. Additionally LBP have the benefit of being extensively used in texture classification.

Techniques for generating SIFT features such as the Local Dense SIFT Features 210 are generally known in the art. Briefly, the region around each keypoint is described by calculating an image gradient and then forming histograms of orientation which measure how strong the gradient is in each direction. The resultant histograms are concatenated to obtain the feature vector.

The Global LBP Histogram Features 215 may be determined as follows. First the input video frame is divided into cells of multiple pixels. For each pixel in a cell, an eight digit binary number is formed by comparing the pixel's intensity to its eight neighbors. Specifically, the pixel being analyzed is treated as the center of a circle comprised of its eight neighbors. If the center pixel's intensity value is greater than that of a neighbor, the corresponding binary digit is a "0"; otherwise, the digit is a "1". Once this is completed for all the pixels in the cell, a histogram is computed over the cell of the frequency of each binary number occurring. This histogram may be optionally normalized. Finally, the histograms of all the cells are concatenated to provide the feature vector for the window.

Continuing with reference to FIG. 2, a Feature Coding Component 220 applies a coding process to convert each of the Local Dense SIFT Features 210 into an m-dimensional code $c_i=[c_{i1} \ldots, C_{im}]^T \in \mathbb{R}^m$. This conversion is performed using a codebook of m entries, $B=[b_1 \ldots, b_n] \in \mathbb{R}^m$ generated offline by a Construct Codebook Component 225. Various techniques may be used for generating the codebook. For example, in some embodiments, k-means clustering performed on a random subset of a large number (e.g. 100,000) of local features, extracted from a training set to form a visual vocabulary. Each feature cluster may be obtained, for example, by utilizing a Euclidean distance based exhaustive nearest-neighbor search or a hierarchical vocabulary tree structure (binary search tree).

Various types of coding processes may be employed by Feature Coding Component 220. Four example coding processes are described herein: Bag of Words (BoW), Sparse Coding, Locality-constrained Linear Coding (LLC), and Locality-constrained Sparse Coding (LSC). In some embodiments, the coding process employed by the Feature Coding Component 220 may help determine some of the parameters of the codebook generated by the Construct Codebook Component 225. For example, for a BoW scheme, the vocabulary tree structure with tree depth of 8 may be used. For Sparse Coding, LLC, and LSC, a k-means of Euclidean distance based exhaustive nearest neighbor search may be used.

Let X be a set of d-dimensional local descriptors extracted from an image (i.e., $X=[x_1 \ldots, x_n] \in \mathbb{R}^m$. Where BoW is employed as the coding process, for a local feature $x_i$, there is one and only one non-zero coding coefficient. The non-zero coding coefficient corresponds to the nearest visual word subject to a predefined distance. When the Euclidean distance is adopted, the code $c_i$ may be calculated as:

$$c_{ij} = \begin{cases} 1 & \text{if } j - \mathrm{argmin}_{j=1,\ldots,n} \|x_i - b_i\|_2^2 \\ 0 & \text{otherwise} \end{cases} \quad (1)$$

In the Sparse Coding scheme, each local feature $x_i$ is represented by a linear combination of a sparse set of basis vectors in the codebook. The coefficient vector $c_i$ is obtained by solving an $l_1$-norm regularized problem:

$$c_i = \arg\min \|x_i - Bc_i\|_2^2 + \lambda\|c_i\|_1$$

$$\text{s.t. } 1^T c_i = 1, \forall i \quad (2)$$

where $\|\cdot\|_1$ denotes the $l_1$-norm of the vector. The constraint $1^T c_i=1$ follows the requirements of the sparse code.

Unlike Sparse Coding, LLC enforces codebook locality instead of sparsity. This leads to smaller coefficients for basis vectors farther away from $x_i$. The code $c_i$ is computed by solving the following regularized least squares error:

$$c_i = \arg\min \|x_i - Bc_i\|_2^2 + \lambda\|d_i \odot c_i\|_2^2$$

$$\text{s.t. } 1^T c_i = 1, \forall i \quad (3)$$

where $\odot$ denotes the element-wise multiplication and $d_i \in \mathbb{R}^m$ is the locality adaptor that gives different freedom for each basis vector proportional to its similarity to the input descriptor $x_i$. Specifically, $$d_i = \frac{dis(x_i, B)}{\sigma} \quad (4)$$

where $dis(x_i,B)=[dis(x_i,b_1) \ldots dis(x_i, b_m)]^T$, and $dis(x_i, b_j)$ is the Euclidean distance between $x_i$ and $b_j$. The value of $\sigma$ is used for adjusting the weight decay speed for local adaptation.

The LSC feature coding method compares favorably to conventional methods in that it not only enforces code sparsity for better discriminative power, but also preserves code locality in the sense that each descriptor is best coded within its local-coordinate system. Specifically, the LSC code can be formulated as:

$$c_i = \operatorname{argmin} \|x_i - Bc_i\|_2^2 + \lambda \|d_i \odot c_i\|_1 \quad (5)$$
$$\text{s.t. } 1^T c_i = 1, \forall i$$

Although various algorithms exist for solving the conventional sparse coding problem, it becomes a significantly challenging optimization problem due to the locality weight vector $d_i$. In some embodiments, the Alternating Direction Method of Multipliers (ADMM) method is used to solve Equation 5. First, a dummy variable $y_i \in \mathbb{R}^m$ is introduced so that Equation 5 may be reformulated as:

$$\min_{c_i} \|x_i - Bc_i\|_2^2 + \lambda \|d_i \odot y_i\|_1 \quad (6)$$
$$\text{s.t. } 1^T y_i = 1$$
$$c_i = y_i$$

Then, we can form the augmented Lagrangian of the above objective, which becomes $$\min_{c_i, y_i} \mathcal{L}(c_i, y_i) = \|x_i - By_i\|_2^2 + \lambda \|d_i \odot c_i\|_1 + \quad (7)$$
$$\mu \|c_i - y_i\|_2^2 + \rho^T(c_i - y_i) + \mu \|1^T y_i - 1\|_2^2 + \gamma(1^T y_1 - 1)$$

The ADMM includes three iterations:

$$y_i^{t+1} = \arg\min_{y_i} \mathcal{L}(y_i, c_i^t, \rho^t, \gamma^t) \quad (8a)$$

$$c_i^{t+1} = \arg\min_{c_i} \mathcal{L}(y_i^{t+1}, c_i, \rho^t, \gamma^t) \quad (8b)$$

$$\rho^{t+1} = \rho^t + \mu(c_i - y_i), \gamma^{t+1} = \gamma^t + \mu(1^T y_i - 1) \quad (8c)$$

which allows the original problem to be broken into a sequence of sub-problems. In sub-problem 8a, we are minimizing $\mathcal{L}$ ($H_i$, $c_i^t$, $\rho^t$, $\gamma^t$) w.r.t. only $y_i$ and the $l_1$-penalty $\|d_i \odot c_i\|_1$ disappears from the objective making it a very efficient and simple least-squares regression problem. In sub-problem 8b, we are minimizing $\mathcal{L}$ ($y_i^{t+1}$, $c_i$, $\rho^t$, $\gamma^t$) w.r.t. only $c_i$, and the term $\|x_1-By_i\|_2^2+\mu\|1^T y_i-1\|_2^2+\gamma(1^T Y_i-1)$ disappears allowing $c_i$ to be solved independently across each element. This now allows soft-thresholding to be used more efficiently. The current estimates of $y_i$ and $c_i$ are then combined in sub-problem 8c to update the current estimate of the Lagrangian multipliers $\rho$ and $\gamma$. Note that $\rho$ and $\gamma$ play a special role here, as they allow us to employ an imperfect estimate of $\rho$ and $\gamma$ when solving for both $y_i$ and $c_i$. For convenience, the following soft-thresholding (shrinkage) operator: may be employed:

$$S_\epsilon[x] = \begin{cases} x - \epsilon & \text{if } x > \epsilon \\ x + \epsilon & \text{if } x < -\epsilon \\ 0 & \text{otherwise} \end{cases} \quad (9)$$

The Classification Components 235, 245 identify one or more class labels for the final image representation based on one or more pre-defined criteria. These class labels may provide an indication of, for example, whether a particular tissue is malignant or benign. Additionally, in some embodiments, the class labels may provide an indication of healthy tissue. The Classification Components 235, 245 utilize one or more classifier algorithms which may be trained and configured based on the clinical study. For example, in some embodiments, the classifier is trained using a brain tumor dataset, such that it can label images as either glioblastoma or meningioma. Various types of classifier algorithms may be used by the Classification Components 235, 245 including, without limitation, support vector machines (SVM), k-nearest neighbors (k-NN), and random forests. Additionally, different types of classifiers can be used in combination. For example, in one embodiment the First Classification Component 235 is an SVM Classifier and the Second Classification Component 245 is a random forest classifier. The output confidences from each representation-classifier combinations are then merged (e.g., using a multiplicative fusion algorithm or weighted average) and the decision for a frame is obtained.

As one example of implementation of the Classification Components 235, 245, in some embodiments, the quantitized features resulting from the Feature Coding Component 220 are used to train an SVM classifier (e.g., with a radial basis function kernel or linear kernel). The parameters of the SVM classifier are selected using a coarse grid search algorithm. The Global LBP Histogram Features 215 are used directly to train a random forest classifier with 8 trees with a maximum depth of 16 levels for each tree.

To illustrate application of the Brain Tumor Classification Process 200, consider a dataset of endomicroscopic videos collected using a CLE Device (see, e.g., FIG. 1) that is inserted inside the patients' brain for examining brain tumor tissues. This collection may result in a set of videos for Glioblastoma and a set of videos for Meningioma. One example of the images collected in such videos is provided in FIG. 3. Notice that some frames with low image texture information are not clinically interesting or not discriminative for image classification. Image entropy may be used to measure the "informativeness" of an image region (i.e., the amount of information contained in an image). Those images with image entropy values which are lower than a predefined threshold may be excluded from the evaluation.

Figure 5:
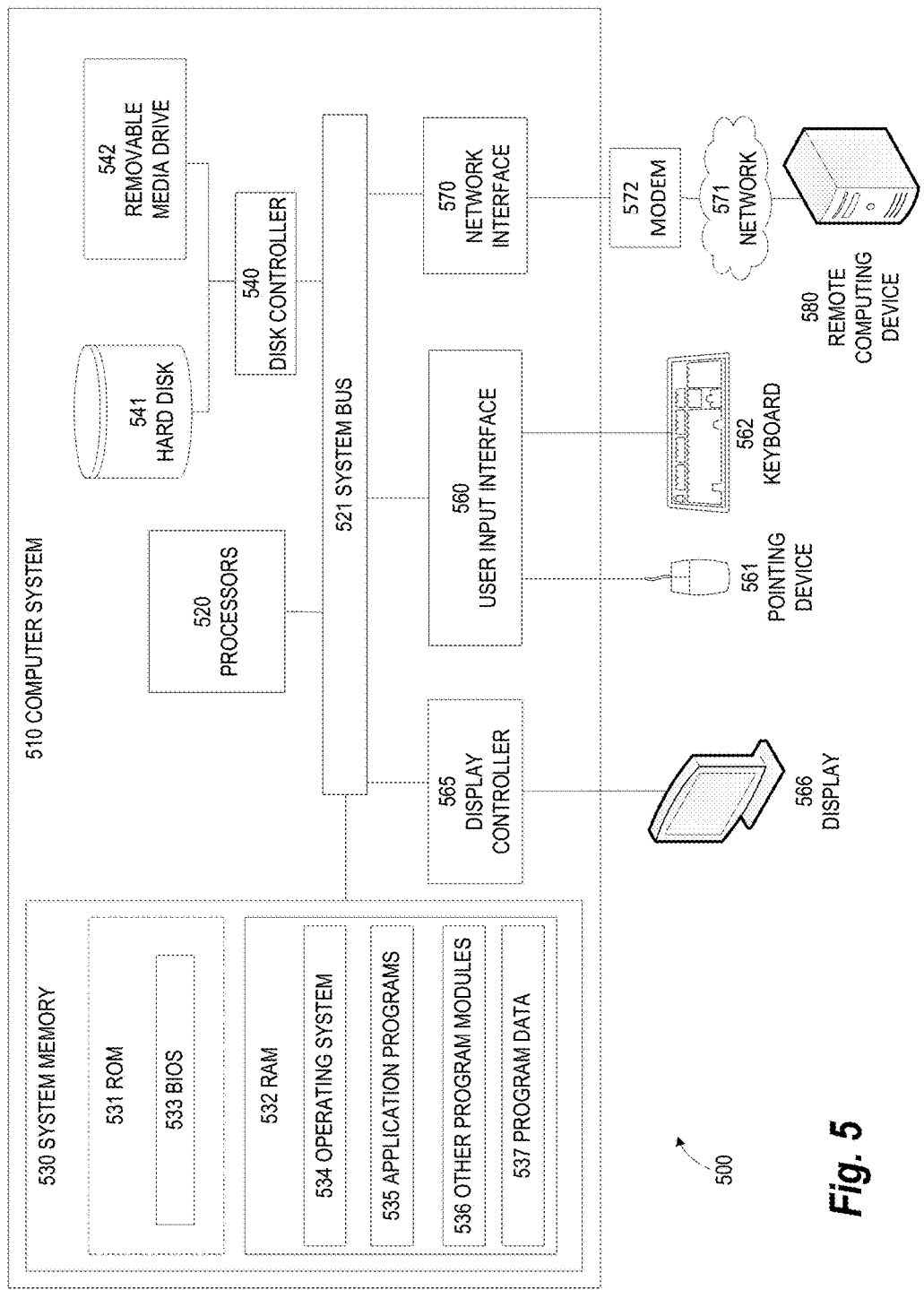
FIG. 5 illustrates an exemplary computing environment, within which embodiments of the invention may be implemented.

FIG. 5 illustrates an exemplary computing environment 500 within which embodiments of the invention may be implemented. For example, this computing environment 500 may be used to implement one or more of devices shown in FIG. 1 and execute the Brain Tumor Classification Process 200 described in FIG. 2. The computing environment 500 may include computer system 510, which is one example of a computing system upon which embodiments of the invention may be implemented. Computers and computing environments, such as computer system 510 and computing environment 500, are known to those of skill in the art and thus are described briefly here.

As shown in FIG. 5, the computer system 510 may include a communication mechanism such as a bus 521 or other communication mechanism for communicating information within the computer system 510. The computer system 510 further includes one or more processors 520 coupled with the bus 521 for processing the information. The processors 520 may include one or more central processing units (CPUs), graphical processing units (GPUs), or any other processor known in the art.

The computer system 510 also includes a system memory 530 coupled to the bus 521 for storing information and instructions to be executed by processors 520. The system memory 530 may include computer readable storage media in the form of volatile and/or nonvolatile memory, such as read only memory (ROM) 531 and/or random access memory (RAM) 532. The system memory RAM 532 may include other dynamic storage device(s) (e.g., dynamic RAM, static RAM, and synchronous DRAM). The system memory ROM 531 may include other static storage device(s) (e.g., programmable ROM, erasable PROM, and electrically erasable PROM). In addition, the system memory 530 may be used for storing temporary variables or other intermediate information during the execution of instructions by the processors 520. A basic input/output system 533 (BIOS) containing the basic routines that help to transfer information between elements within computer system 510, such as during start-up, may be stored in ROM 531. RAM 532 may contain data and/or program modules that are immediately accessible to and/or presently being operated on by the processors 520. System memory 530 may additionally include, for example, operating system 534, application programs 535, other program modules 536 and program data 537.

The computer system 510 also includes a disk controller 540 coupled to the bus 521 to control one or more storage devices for storing information and instructions, such as a hard disk 541 and a removable media drive 542 (e.g., floppy disk drive, compact disc drive, tape drive, and/or solid state drive). The storage devices may be added to the computer system 510 using an appropriate device interface (e.g., a small computer system interface (SCSI), integrated device electronics (IDE), Universal Serial Bus (USB), or FireWire).

The computer system 510 may also include a display controller 565 coupled to the bus 521 to control a display 566, such as a cathode ray tube (CRT) or liquid crystal display (LCD), for displaying information to a computer user. The computer system includes an input interface 560 and one or more input devices, such as a keyboard 562 and a pointing device 561, for interacting with a computer user and providing information to the processor 520. The pointing device 561, for example, may be a mouse, a trackball, or a pointing stick for communicating direction information and command selections to the processor 520 and for controlling cursor movement on the display 566. The display 566 may provide a touch screen interface which allows input to supplement or replace the communication of direction information and command selections by the pointing device 561.

The computer system 510 may perform a portion or all of the processing steps of embodiments of the invention in response to the processors 520 executing one or more sequences of one or more instructions contained in a memory, such as the system memory 530. Such instructions may be read into the system memory 530 from another computer readable medium, such as a hard disk 541 or a removable media drive 542. The hard disk 541 may contain one or more datastores and data files used by embodiments of the present invention. Datastore contents and data files may be encrypted to improve security. The processors 520 may also be employed in a multi-processing arrangement to execute the one or more sequences of instructions contained in system memory 530. In alternative embodiments, hardwired circuitry may be used in place of or in combination with software instructions. Thus, embodiments are not limited to any specific combination of hardware circuitry and software.

As stated above, the computer system 510 may include at least one computer readable medium or memory for holding instructions programmed according to embodiments of the invention and for containing data structures, tables, records, or other data described herein. The term "computer readable medium" as used herein refers to any medium that participates in providing instructions to the processor 520 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 541 or removable media drive 542. Non-limiting examples of volatile media include dynamic memory, such as system memory 530. Non-limiting examples of transmission media include coaxial cables, copper wire, and fiber optics, including the wires that make up the bus 521. Transmission media may also take the form of acoustic or light waves, such as those generated during radio wave and infrared data communications.

The computing environment 500 may further include the computer system 510 operating in a networked environment using logical connections to one or more remote computers, such as remote computer 580. Remote computer 580 may be a personal computer (laptop or desktop), a mobile device, a server, a router, a network PC, a peer device or other common network node, and typically includes many or all of the elements described above relative to computer system 510. When used in a networking environment, computer system 510 may include modem 572 for establishing communications over a network 571, such as the Internet. Modem 572 may be connected to bus 521 via user network interface 570, or via another appropriate mechanism.

Network 571 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 510 and other computers (e.g., remote computer 580). The network 571 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 571.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

The invention claimed is:

1. A method for performing cellular classification, the method comprising:
generating a plurality of local dense Scale Invariant Feature Transform (SIFT) features based on a set of input images;
converting the plurality of local dense SIFT features into a multi-dimensional code using a feature coding process;
using a first classification component to generate first output confidence values based on the multi-dimensional code;
generating a plurality of global Local Binary Pattern Histogram (LBP-H) features based on the set of input images;
using a second classification component to generate second output confidence values based on the plurality of LBP-H features;
merging the first output confidence values and the second output confidence values using a fusion algorithm to yield merged output confidence values; and
classifying each of the set of input images as one of a plurality of cell types using the merged output confidence values, wherein the fusion algorithm is a multiplicative fusion algorithm.

2. The method of claim 1, further comprising:
acquiring a plurality of input images;
calculating an entropy value for each of the plurality of input images, each entropy value representative of an amount of texture information in a respective image;
identifying one or more low-entropy images in the set of input images, wherein the one or more low-entropy images are each associated with a respective entropy value below a threshold value; and
generating the set of input images based on the plurality of input images, wherein the set of input images excludes the one or more low-entropy images.

3. The method of claim 2, wherein the plurality of input images are acquired using an endomicroscopy device during a medical procedure.

4. The method of claim 2, wherein the plurality of input images are acquired using a digital holographic microscopy device during a medical procedure.

5. The method of claim 1, wherein the feature coding process performs a bag of words coding process.

6. The method of claim 5, wherein the bag of words coding process comprises:
randomly selecting a predetermined percentage of descriptors from a training split;
performing k-means clustering to construct a plurality of different vocabularies;
using the plurality of different vocabularies to quantize the SIFT features in each input image included in the set of input images to yield a quantized representation of the SIFT features,
wherein the multi-dimensional code is the quantized representation.

7. The method of claim 1, wherein the first classification component is a Support Vector Machine (SVM) classifier.

8. The method of claim 7, wherein the multi-dimensional code is used to train the SVM classifier with a radial basis function (RBF) kernel.

9. The method of claim 7, wherein the multi-dimensional code is used to train the SVM classifier with a linear kernel.

10. The method of claim 1, wherein the second classification component is a Random Forest classifier with a plurality of trees and a maximum depth of a plurality of levels for each of the plurality of trees.

11. A method for performing cellular classification during a medical procedure, the method comprising:
prior to the medical procedure, performing a training process comprising:
training a first classification component based on a plurality of local dense SIFT features associated with a plurality of training images, and
training a second classification component based on a plurality of global LBP-H features associated with the plurality of training images; and
during the medical procedure, performing a cell classification process comprising:
acquiring an input image using an endomicroscopy device,
using the first classification component to generate first output confidence values based on SIFT features associated with the input image, using the second classification component to generate second output confidence values based on LBP-H features associated with the input image, multiplying the first output confidence values and the second output confidence values to yield merged output confidence values; and identifying a class label corresponding to the input image based on the merged output confidence values, and presenting the class label on a display operably coupled to the endomicroscopy device.

12. The method of claim 11, wherein the class label provides an indication of whether biological material in the input image is healthy, malignant, or benign.

13. The method of claim 11, wherein the first classification component is an SVM classifier.

14. The method of claim 13, wherein the second classification component is a Random Forrest classifier.

15. A system performing cellular classification, the system comprising:

an endomicroscopy device including a probe configured to acquire a set of input images during a medical procedure;

an imaging computer configured to perform a cellular classification process during the medical procedure, the cellular classification process comprising:

using a first classification component to generate first output confidence values based on SIFT features associated with the set of input images, using a second classification component to generate second output confidence values based on LBP-H features associated with the set of input images, multiplying the first output confidence values and the second output confidence values to yield merged output confidence values; and identifying one or more cellular class labels corresponding to the set of input images based on the merged output confidence values, and a display configured to present the one or more cellular class labels during the medical procedure.

16. The system of claim 15, wherein the endomicroscopy device is a Confocal Laser Endo-microscopy device.

17. The system of claim 15, wherein the endomicroscopy device is a Digital Holographic Microscopy device.

18. The system of claim 15, wherein the first classification component is a SVM classifier.

19. The system of claim 18, wherein the second classification component is a Random Forrest classifier.

* * * * *